(12) United States Patent
Sandhu

(10) Patent No.: US 6,479,297 B1
(45) Date of Patent: Nov. 12, 2002

(54) SENSOR DEVICES, METHODS AND SYSTEMS FOR DETECTING GAS PHASE MATERIALS

(75) Inventor: Gurtej S. Sandhu, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 09/652,634

(22) Filed: Aug. 31, 2000

(51) Int. Cl.[7] ............................................. G01N 27/416
(52) U.S. Cl. ..................... 436/151; 436/149; 422/90; 422/98; 422/108; 422/119
(58) Field of Search ................... 436/151, 149; 422/88, 90, 98, 108, 119

(56) References Cited

U.S. PATENT DOCUMENTS

| | | | | |
|---|---|---|---|---|
| 3,890,703 A | * | 6/1975 | Frazee et al. | 29/621 |
| 4,433,320 A | * | 2/1984 | Murata et al. | 338/35 |
| 4,677,416 A | * | 6/1987 | Nishimoto et al. | 338/35 |
| 5,147,737 A | * | 9/1992 | Post et al. | 429/94 |
| 5,857,250 A | | 1/1999 | Riley et al. | |
| 5,906,726 A | | 5/1999 | Schneider et al. | |
| 6,280,604 B1 | * | 8/2001 | Allen et al. | 205/777.5 |

OTHER PUBLICATIONS

Kawahara et al., "(Ba,Sr)TiO$_3$ Films Prepared by Liquid Source Chemical Vapor Deposition on Ru Electrodes," *Jpn. J. Appl. Phys.*, 35(Part 1, No. 9B):4880–4885 (1996).

* cited by examiner

*Primary Examiner*—Arlen Soderquist
*Assistant Examiner*—Yelena Gakh
(74) *Attorney, Agent, or Firm*—Mueting, Raasch & Gebhardt, P.A.

(57) ABSTRACT

Sensor arrays, methods, and systems for detecting the presence of gas phase materials by the formation of films based on the gas phase material are disclosed. The gas phase materials preferentially deposit conductive films on receptor materials that can be detected. The invention may also provide for increased sensitivity to the deposition of conductive materials through the use of closely spaced conductive electrodes interconnected by lines of receptor material. Examples of gas phase materials that may be detected include $RuO_4$, $IrO_4$ and $RhO_4$.

57 Claims, 3 Drawing Sheets

SENSOR DEVICES, METHODS AND SYSTEMS FOR DETECTING GAS PHASE MATERIALS

FIELD OF THE INVENTION

The present invention relates to the sensors for the detection of selected materials. More particularly, the present invention pertains to sensors for the detection of gas phase materials.

BACKGROUND

In the fabrication of integrated circuits, various layers of the same or different materials are used. For example, during the formation of semiconductor devices, such as dynamic random access memories (DRAMs), static random access memories (SRAMs), ferroelectric (FE) memories, etc., a variety of conductive and non-conductive materials are used to construct storage cell capacitors and also may be used in interconnection structures, e.g., conductive layers of contact holes, vias, etc.

These materials are typically supplied in a gas phase conducive to the formation of a film on a surface. When supplied in the gas phase, many of these materials may become toxic or otherwise harmful to health. As a result, it may be important to monitor where these materials are found and the concentrations in which they are found. Furthermore, because the effects may be cumulative, i.e., repeated exposure to low levels of the selected materials may be additive, it may be important to provide sensors and detection methods that are capable of measuring for cumulative exposure levels in addition to real-time exposure.

Semiconductor device manufacturing is one example of an environment in which the monitoring of exposure to potentially harmful materials can be advantageous. For example, various metals, metallic compounds, metal oxides, etc. are used to manufacture various structures used in semiconductor devices. A number of these materials may pose health risks based on exposure to the materials in the gas phase.

For example, ruthenium oxide and ruthenium have recently been employed in semiconductor devices because these materials are electrically conductive, conducive to conformal deposition, and they are easily etched. For example, the article entitled, "(Ba,Sr)TiO$_3$ Films Prepared by Liquid Source Chemical Vapor Deposition on Ru Electrodes," by Kawahara et al., Jpn. J. Appl. Phys., Vol. 35 (1996), Part 1, No. 9B (September 1996), pp. 4880–4885, describes the use of ruthenium and ruthenium oxide for forming electrodes in conjunction with high dielectric constant materials. It is, however, known that gaseous ruthenium tetraoxide (RuO$_4$) is toxic at very low levels, e.g., about 1 part per billion (ppb). Monitoring of exposure to ruthenium tetraoxide is, therefore, both important due to its toxicity and difficult due to the low exposure levels at which the toxicity becomes an issue.

For example, many detection systems or procedures for many different gas phase materials rely on chemically sensitive tapes. Stains are produced due to chemical reactions occurring on the tapes in response to chemical exposure and those stains can then be detected. Problems with such tapes may, however, include sensitivity to different chemicals.

With respect to ruthenium tetraoxide, some useful chemically sensitive tapes are also sensitive to other chemicals such as oxidizing agents. As a result, the tapes typically cannot be used to accurately detect exposure to ruthenium oxide. Other tapes may detect ruthenium oxide, but could not be used to accurately detect at desired exposure levels.

SUMMARY OF THE INVENTION

The present invention provides sensors for and methods of detecting the presence of gas phase materials by detecting the formation of films based on the gas phase material. Advantageously, some gas phase materials preferentially deposit on receptor materials. As a result, selective detection of those gas phase materials can be obtained by detecting films deposited on the receptor materials. In addition to selectivity, the present invention may also provide for continuous film deposition on a receptor material at the minimum, or close to minimum, exposure levels.

Further advantages of the present invention are an increased sensitivity to the deposition of conductive materials through the use of closely spaced conductive electrodes interconnected by lines of receptor material. The gas phase material preferentially deposits on the receptor material as compared to the surrounding substrate surface. That preferential deposition may improve sensitivity of the sensor by reducing the areas on which the gas phase material will form conductive layers.

In one aspect, the present invention provides for detection of gaseous ruthenium oxide (RuO$_4$) which preferentially deposits on a variety of surfaces, e.g., polypropylene. The deposited film includes elemental ruthenium (Ru) and/or ruthenium oxide (RuO$_2$) which exhibit relatively high electrical conductivity. As a result, detection of gaseous ruthenium oxide may be performed by monitoring electrical conductivity across a detection surface. Exposure levels may be determined based on the increases in electrical conductivity.

Further advantages of the present invention may include reduced sensitivity to environmental contaminants because relatively few environmental contaminants will deposit on any surface in the form of, e.g., an electrically conductive film. In addition, heating the detection surface or otherwise treating the detection surface during or before use may further improve sensitivity to environmental contaminants by reducing or eliminating deposition of environmental moisture and most organic materials.

Detection of the selected material or materials in the gaseous phase may serve a variety of purposes including the detection of toxic/hazardous materials to insure proper industrial safety standards; to monitor reaction levels for process control; to determine the integrity of containment systems; etc.

In one aspect, the present invention provides a sensor array for detecting a gas phase material, the array including a substrate surface; at least one line of receptor material on the substrate surface, wherein the gas phase material preferentially deposits on the receptor material as compared to the substrate surface surrounding the receptor material; a serpentine electrode on the substrate surface, the serpentine electrode including a plurality of U-shaped segments spaced along the line of receptor material and opening in alternating first and second opposing directions along the line of receptor material; and a comb electrode on the substrate surface, the comb electrode including a plurality of tines, wherein at least some of the tines extend into at least some of the U-shaped segments opening in the first direction, and further wherein at least some of the tines extending into the U-shaped segments intersect the line of receptor material.

In another aspect, the present invention provides a sensor array for detecting a gas phase material, the array including a substrate surface; at least two lines of receptor material on the substrate surface, wherein the gas phase material preferentially deposits on the receptor material as compared to the substrate surface surrounding the receptor material; a serpentine electrode on the substrate surface, the serpentine electrode including a plurality of U-shaped segments spaced along the lines of receptor material and opening in alternating first and second opposing directions along the lines of receptor material; and a comb electrode on the substrate surface, the comb electrode including a plurality of tines, wherein at least some of the tines extend into at least some of the U-shaped segments opening in the first direction, and further wherein at least some of the tines extending into the U-shaped segments intersect the lines of receptor material.

In another aspect, the present invention provides a sensor array for detecting a gas phase material, the array including a substrate surface; at least one line of receptor material on the substrate surface, wherein the gas phase material preferentially deposits on the receptor material as compared to the substrate surface surrounding the receptor material; a serpentine electrode on the substrate surface, the serpentine electrode including a plurality of U-shaped segments spaced along the line of receptor material and opening in alternating first and second opposing directions along the line of receptor material; a first comb electrode on the substrate surface, the first comb electrode including a plurality of tines, wherein at least some of the tines extend into at least some of the U-shaped segments opening in the first direction, and further wherein at least some of the tines extending into the U-shaped segments intersect the line of receptor material; and a second comb electrode on the substrate, the second comb electrode including a plurality of tines, wherein at least some of the tines extend into at least some of the U-shaped segments opening in the second direction, and further wherein at least some of the tines of the second comb electrode extending into the U-shaped segments intersect the line of receptor material.

In another aspect, the present invention provides a sensor array for detecting a gas phase material, the array including a substrate surface; at least two lines of receptor material on the substrate surface, wherein the selected material preferentially deposits on the receptor-material as compared to the substrate surface surrounding the receptor material; a serpentine electrode on the substrate surface, the serpentine electrode including a plurality of U-shaped segments spaced along the lines of receptor material and opening in alternating first and second opposing directions along the lines of receptor material; a first comb electrode on the substrate surface, the first comb electrode including a plurality of tines, wherein at least some of the tines extend into at least some of the U-shaped segments opening in the first direction, and further wherein at least some of the tines extending into the U-shaped segments intersect the lines of receptor material; and a second comb electrode on the substrate, the second comb electrode including a plurality of tines, wherein at least some of the tines extend into at least some of the U-shaped segments opening in the second direction, and further wherein at least some of the tines of the second comb electrode extending into the U-shaped segments intersect the lines of receptor material.

In another aspect, the present invention provides a method of detecting a gas phase material by providing a sensor array including a substrate surface; at least one line of receptor material on the substrate surface, wherein the gas phase material preferentially deposits on the receptor material as compared to the substrate surface surrounding the receptor material; a serpentine electrode on the substrate surface, the serpentine electrode including a plurality of U-shaped segments spaced along the line of receptor material and opening in alternating first and second opposing directions along the line of receptor material; and a comb electrode on the substrate surface, the comb electrode including a plurality of tines, wherein at least some of the tines extend into at least some of the U-shaped segments opening in the first direction, and further wherein at least some of the tines extending into the U-shaped segments intersect the line of receptor material. The method also includes exposing the sensor array to the gas phase material and monitoring electrical conductivity between the serpentine electrode and the comb electrode.

In another aspect, the present invention provides a method of detecting a gas phase material by providing a sensor array including a substrate surface; at least two lines of receptor material on the substrate surface, wherein the gas phase material preferentially deposits on the receptor material as compared to the substrate surface surrounding the receptor material; a serpentine electrode on the substrate surface, the serpentine electrode including a plurality of U-shaped segments spaced along the lines of receptor material and opening in alternating first and second opposing directions along the lines of receptor material; and a comb electrode on the substrate surface, the comb electrode including a plurality of tines, wherein at least some of the tines extend into at least some of the U-shaped segments opening in the first direction, and further wherein at least some of the tines extending into the U-shaped segments intersect the lines of receptor material a substrate surface. The method also includes exposing the sensor array to the gas phase material and monitoring electrical conductivity between the serpentine electrode and the comb electrode.

In another aspect, the present invention provides a method of detecting a gas phase material by providing a sensor array including a substrate surface; at least one line of receptor material on the substrate surface, wherein the gas phase material preferentially deposits on the receptor material as compared to the substrate surface surrounding the receptor material; a continuous serpentine electrode on the substrate surface, the serpentine electrode including a plurality of U-shaped segments spaced along the line of receptor material and opening in alternating first and second opposing directions along the line of receptor material; a first comb electrode on the substrate surface, the first comb electrode including a plurality of tines, wherein at least some of the tines extend into at least some of the U-shaped segments opening in the first direction, and further wherein at least some of the tines extending into the U-shaped segments intersect the line of receptor material; and a second comb electrode on the substrate, the second comb electrode including a plurality of tines, wherein at least some of the tines extend into at least some of the U-shaped segments opening in the second direction, and further wherein at least some of the tines of the second comb electrode extending into the U-shaped segments intersect the line of receptor material. The method also includes exposing the sensor array to the gas phase material and monitoring electrical conductivity between the serpentine electrode and at least one of the first and second comb electrodes.

In another aspect, the present invention provides a method of detecting a gas phase material by providing a sensor array including a substrate surface; at least two lines of receptor material on the substrate surface, wherein the selected material preferentially deposits on the receptor material as compared to the substrate surface surrounding the receptor material; a serpentine electrode on the substrate surface, the serpentine electrode including a plurality of U-shaped segments spaced along the lines of receptor material and opening in alternating first and second opposing directions along the lines of receptor material; a first comb electrode on the substrate surface, the first comb electrode including a plurality of tines, wherein at least some of the tines extend into at least some of the U-shaped segments opening in the first direction, and further wherein at least some of the tines extending into the U-shaped segments intersect the lines of receptor material; and a second comb electrode on the substrate, the second comb electrode including a plurality of tines, wherein at least some of the tines extend into at least some of the U-shaped segments opening in the second direction, and further wherein at least some of the tines of the second comb electrode extending into the U-shaped segments intersect the lines of receptor material. The method further includes exposing the sensor array to the gas phase material and monitoring electrical conductivity between the serpentine electrode and at least one of the first and second comb electrodes.

In another aspect, the present invention provides a system for detecting a gas phase material, the system including a sensor array with a substrate surface; at least one line of receptor material on the substrate surface, wherein the gas phase material preferentially deposits on the receptor material as compared to the substrate surface surrounding the receptor material; a serpentine electrode on the substrate surface, the serpentine electrode including a plurality of U-shaped segments spaced along the line of receptor material and opening in alternating first and second opposing directions along the line of receptor material; and a comb electrode on the substrate surface, the comb electrode including a plurality of tines, wherein at least some of the tines extend into at least some of the U-shaped segments opening in the first direction, and further wherein at least some of the tines extending into the U-shaped segments intersect the line of receptor material. The system further includes a detector in electrical communication with the serpentine electrode and the comb electrode.

In another aspect, the present invention provides a system for detecting a gas phase material, the system including a sensor array with a substrate surface; at least two lines of receptor material on the substrate surface, wherein the gas phase material preferentially deposits on the receptor material as compared to the substrate surface surrounding the receptor material; a serpentine electrode on the substrate surface, the serpentine electrode including a plurality of U-shaped segments spaced along the lines of receptor material and opening in alternating first and second opposing directions along the lines of receptor material; and a comb electrode on the substrate surface, the comb electrode including a plurality of tines, wherein at least some of the tines extend into at least some of the U-shaped segments opening in the first direction, and further wherein at least some of the tines extending into the U-shaped segments intersect the lines of receptor material a substrate surface. The system further includes a detector in electrical communication with the serpentine electrode and the comb electrode.

In another aspect, the present invention includes a system for detecting a gas phase material, the system including a sensor array with a substrate surface; at least one line of receptor material on the substrate surface, wherein the gas phase material preferentially deposits on the receptor material as compared to the substrate surface surrounding the receptor material; a serpentine electrode on the substrate surface, the serpentine electrode including a plurality of U-shaped segments spaced along the line of receptor material and opening in alternating first and second opposing directions along the line of receptor material; a first comb electrode on the substrate surface, the first comb electrode including a plurality of tines, wherein at least some of the tines extend into at least some of the U-shaped segments opening in the first direction, and further wherein at least some of the tines extending into the U-shaped segments intersect the line of receptor material; and a second comb electrode on the substrate, the second comb electrode including a plurality of tines, wherein at least some of the tines extend into at least some of the U-shaped segments opening in the second direction, and further wherein at least some of the tines of the second comb electrode extending into the U-shaped segments intersect the line of receptor material. The system further includes a detector in electrical communication with the serpentine electrode, the first comb electrode and the second comb electrode.

In another aspect, the present invention provides a system for detecting a gas phase material, the system including a sensor array with a substrate surface; at least two lines of receptor material on the substrate surface, wherein the selected material preferentially deposits on the receptor material as compared to the substrate surface surrounding the receptor material; a serpentine electrode on the substrate surface, the serpentine electrode including a plurality of U-shaped segments spaced along the lines of receptor material and opening in alternating first and second opposing directions along the lines of receptor material; a first comb electrode on the substrate surface, the first comb electrode including a plurality of tines, wherein at least some of the tines extend into at least some of the U-shaped segments opening in the first direction, and further wherein at least some of the tines extending into the U-shaped segments intersect the lines of receptor material; and a second comb electrode on the substrate, the second comb electrode including a plurality of tines, wherein at least some of the tines extend into at least some of the U-shaped segments opening in the second direction, and further wherein at least some of the tines of the second comb electrode extending into the U-shaped segments intersect the lines of receptor material. The system further includes a detector in electrical communication with the serpentine electrode, the first comb electrode and the second comb electrode.

These and other features and advantages of the present invention are described below with respect to illustrative embodiments of the invention.

BRIEF DESCRIPTION OF THE DRAWINGS

The present invention will be better understood from reading the following description of illustrative embodiments with reference to the attached drawings, wherein below.

DETAILED DESCRIPTION OF ILLUSTRATIVE EMBODIMENTS OF THE INVENTION

Figure 1:
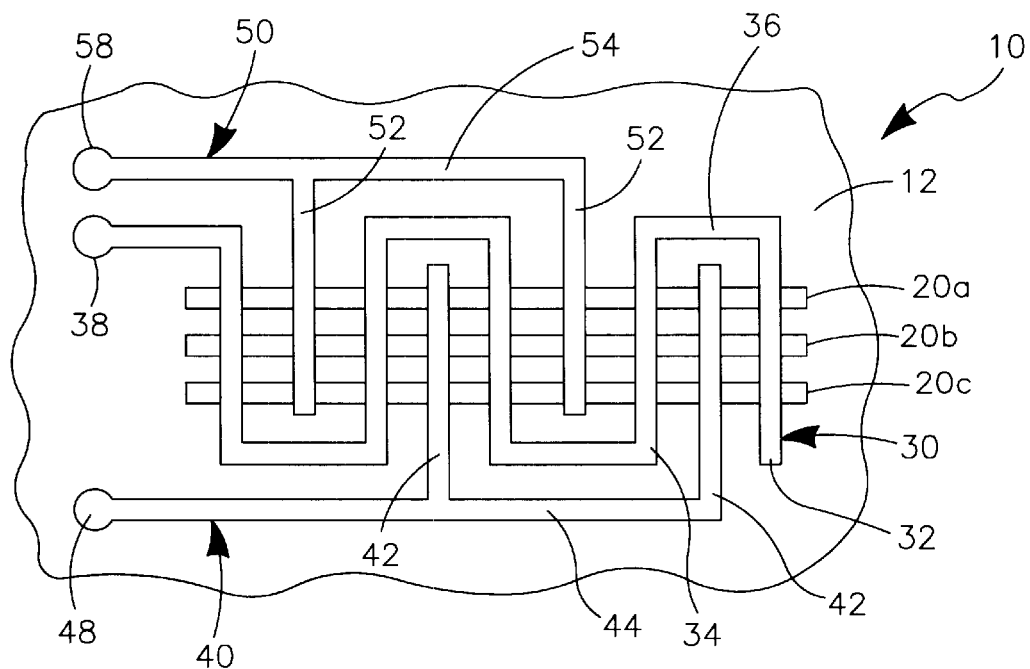
FIG. 1 illustrates one sensor array according to the present invention.

The present invention provides devices and methods for the monitoring of gas phase material levels by detecting films formed from the gas phase materials on receptor materials. One example of an industry using gas phase materials is in the production of semiconductor and other micro-scale devices. Processing steps such as wet etching, dry etching, chemical vapor deposition, etc., may often use or produce gas phase materials that may be, e.g., toxic, corrosive, irritants, etc. Detection of the gas phase materials may be desirable for safety, environmental, or process control purposes. Examples of gas phase materials that may be detected include, but are not limited to, $RuO_4$, $IrO_4$ and $RhO_4$.

Some methods and devices for detecting gas phase materials including, e.g., ruthenium, is described in U.S. patent application Ser. No. 09/388,286, filed on Sep. 1, 1999, entitled DETECTION OF GAS PHASE MATERIALS. The present invention provides further advantages.

The present invention capitalizes on the tendencies of the gas phase materials to deposit or form films or coatings on receptor materials. In some instances, the gas phase materials will preferentially deposit on receptor materials that have a particular structure. By relying on preferential deposition tendencies, the present invention offers advantages in monitoring for the materials. For example, continuous film deposition of the gas phase materials on the receptor material may be obtained at minimum, or close to minimum, exposure levels.

As formed on the receptor materials as a result of exposure to the gas phase material, the film may consist essentially of the gas phase material, the film may include one or more constituents in the gas phase material, or the film may be formed of the gas phase material or one or more constituents thereof in addition with other materials, in e.g., a matrix, dispersion, etc.

It may be preferred that, as deposited, the gas phase material or materials form an electrically conductive film or coating on a receptor material. By detecting changes in the electrical properties (e.g., conductivity, capacitance, etc.) between at least two electrodes on the receptor material, the present invention provides the ability to detect the presence of the gas phase materials.

Typically, deposition rate will be dependent on a variety of factors including, but not limited to the concentration of the selected material in the gaseous state, the properties of the receptor material (e.g., temperature, morphology, etc.), and the environment in which the receptor material is located (e.g., temperature, pressure, etc.). Other variables affecting deposition rate may include deposition-enhancing factors, such as laser-assisted deposition, plasma generation, etc. Regardless of the variables in deposition rate, however, it is preferred that the rate of change in conductivity correlate with exposure levels.

To further enhance sensitivity to the gas phase material being detected, the receptor material is provided in selected areas on a substrate surface. Conductive electrodes are then located over the receptor material. The gas phase material preferentially deposits on the receptor material as compared to the substrate surface surrounding the receptor material. As a result, sensitivity is enhanced because the gas phase material deposited on the receptor material is concentrated on the receptor material, thereby exhibiting faster increases in conductivity as compared to sensors in which the entire surface between electrodes receives a deposited gas phase material.

In addition to providing receptor material in only selected areas on the substrate surface, sensitivity is further enhanced in connection with the present invention by providing at least two electrodes that intersect the receptor material in multiple locations forming a sensor array. The sensor array thus formed provides an increased number of potential conductive paths between electrodes that can be formed by deposition of the gas phase material. As the potential conductive paths are connected during deposition of the gas phase material on the receptor material, the electrical conductivity between the electrodes is increased. Monitoring for that increased electrical conductivity can provide for detection of te gas phase material.

Exemplary embodiments of sensor arrays and systems using the arrays are described below in connection with the figures.

FIG. 1 is a schematic diagram of one sensor array 10 according to the present invention. The sensor array 10 includes three lines 20a, 20b, 20c (collectively referred to herein as lines 20) of receptor material on a substrate surface 12. Although three lines 20 are illustrated, it should be understood that only one line, only two lines, or more than three lines could be provided in a sensor array 10 according to the present invention.

It may be preferred that the lines 20 of receptor material do not intersect with each other. The illustrated lines 20 may also be, optionally, straight, parallel to each other, and/or of consistent width along their length.

The array 10 also includes a serpentine electrode 30, first comb electrode 40, and an optional second comb electrode 50. The serpentine electrode 30 includes U-shaped segments spaced along the lines 20 of receptor material, the U-shaped segments opening in alternating first and second opposing directions on opposite sides of the lines 20 of receptor material. In FIG. 1, those opposing directions are towards the top of the sheet and bottom of the sheet. One of the U-shaped segments in serpentine electrode 30 is formed, in the illustrated embodiment, by legs 32 and 34, which are connected by a base segment 36. Other shapes may be envisioned, such as a U-shape with a rounded base segment 36.

The serpentine electrode 30 may include, in the illustrated embodiment, a connection pad 38 to which a sensor can be connected as will be described in more detail below.

A first comb electrode 40 is also illustrated in FIG. 1 as a part of the array 10. The comb electrode 40 includes tines 42 extending into the U-shaped segments formed by the serpentine electrode 30. The tines 42 intersect the lines 20 of receptor material as they pass through the U-shaped segments of the serpentine electrode 30. The tines 42 are connected by a spine 44 that leads out, in the illustrated embodiment, to an optional connection pad 48 for connection to a sensor.

Also illustrated in FIG. 1 is an optional second comb electrode 50 including tines 52 connected to a spine 54 that leads out to an optional connection pad 58. The tines 52 of the second comb electrode 50 extend into the U-shaped segments of the serpentine electrode 30 that open in the opposite direction from those in which tines 42 of the first comb electrode 40 are located.

The serpentine electrode 30, and comb electrodes 40 and 50 are separated from each other in the illustrated array 10 by the lines 20 of receptor material and the substrate surface 12 that surrounds the lines 20 of receptor material; Both the lines 20 of receptor material and the substrate surface 12 preferably electrically isolates the serpentine electrode 30 from the comb electrodes 40 and 50 such that, e.g., current is prevented from flowing between the serpentine electrode 30 and the comb electrodes 40 and 50. Alternatively, the lines 20 of receptor material and the substrate surface 12 may provide low level conductivity between the serpentine electrode 30 and either or both of the comb electrodes 40 and 50, with the conductivity increasing as a conductive film is formed on the lines 20 of receptor material from the gas phase material.

Selection of the receptor material used in lines 20 relative to the substrate surface 12 is influenced by the desired preferential nature of the deposition process. The receptor material should preferentially attract deposition of the gas phase material to be detected relative to any of the other materials exposed on the surface of the array 10 to enhance sensitivity of the detection. It may further be preferred that the substrate surface 12 and/or electrodes 30, 40 and 50 be provided of materials that allow for relatively free migration of the gas phase material deposited thereon to the receptor material forming lines 20. As a result, film formation of the gas phase material on the lines 20 of receptor material may be enhanced. That enhanced film formation may improve detection sensitivity. Illustrative examples of suitable receptor materials on which gaseous ruthenium oxide preferentially deposits include, but are not limited to, polypropylene, fluoropolymers, 1,1,1,3,3,3-hexamethyldisiloxane (HMDS) coated surfaces, amorphous carbon, parylene, etc.

The substrate surface 12 surrounding the receptor material in lines 20 may include a variety of materials that preferably exhibit a tendency to allow relatively free migration of the gas phase material deposited thereon (relative to the receptor materials in lines 20). Examples of suitable materials include, but are not limited to, e.g., inorganic materials such as quartz, silicon oxide, silicon nitride, borophosphosilicate glass, etc.

Alternatively, deposition of the gas phase material on the receptor material and/or substrate surface 12 may be affected by surface morphology, e.g., whether the surfaces are relatively smooth or rough. A rough surface may be structured by, e.g., molding, or randomly roughened by e.g., sandblasting, chemical etching, etc.

In addition to the materials selected for the sensor array 10, the distances between the various features on the array 10, e.g., between the serpentine electrode 30 and the comb electrodes 40 and 50, may be used to control the sensitivity of the detector 10 to a particular gas phase material. Other dimensions that may affect sensitivity of the sensor array 10 include the widths of the various features on the array 10. Factors affecting the selection of an appropriate dimensions may include, but are not limited to: resistivity of the deposited film/coating (from the gas phase material), resistivity of the receptor material before deposition, ambient conditions (humidity, temperature, etc.), temperature, etc.

In use, the sensor array 10 is connected to a detector (not shown in FIG. 1) that is capable of detecting a change in conductivity between the serpentine electrode 30 and one or both of the comb electrodes 40 and 50 across the lines 20 of receptor material as a result of deposition of one or more gas phase materials in the form of a film or coating on the receptor material. It is preferred that low level depositions of a conductive film on the lines 20 of receptor material can produce a finite and accurately measurable change in current flow between the electrodes.

Figure 2:
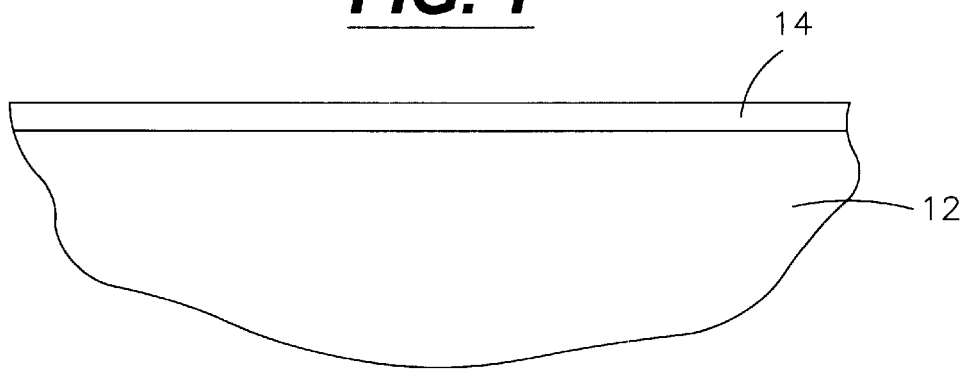
FIG. 2 is a cross-sectional view of the sensor array during one manufacturing process.
Figure 3:
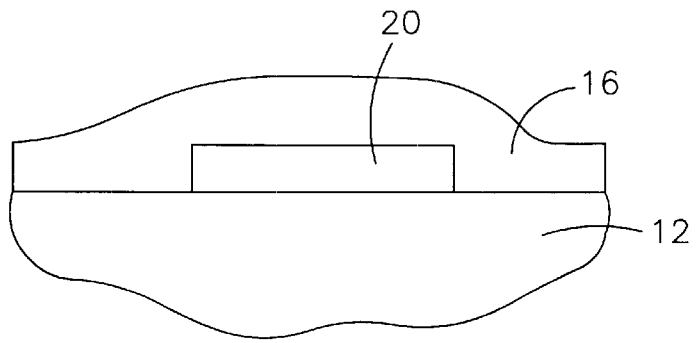
FIG. 3 is a cross-sectional view illustrating the relationship between the substrate, receptor lines and electrodes on preferred sensor arrays according to the present invention.

Turning now to FIG. 2, it may be desirable to manufacture the sensor array 10 by first depositing a layer 14 of the receptor material on the substrate surface 12. That layer 14 can then be patterned using known processes to form, e.g., lines 20 of receptor material as seen in FIG. 1. Following formation of the lines 20 from receptor material 14, the conductive electrode material 16 used to form the electrodes can be provided over the receptor material in the line 20 as illustrated in FIG. 3.

Figure 4:
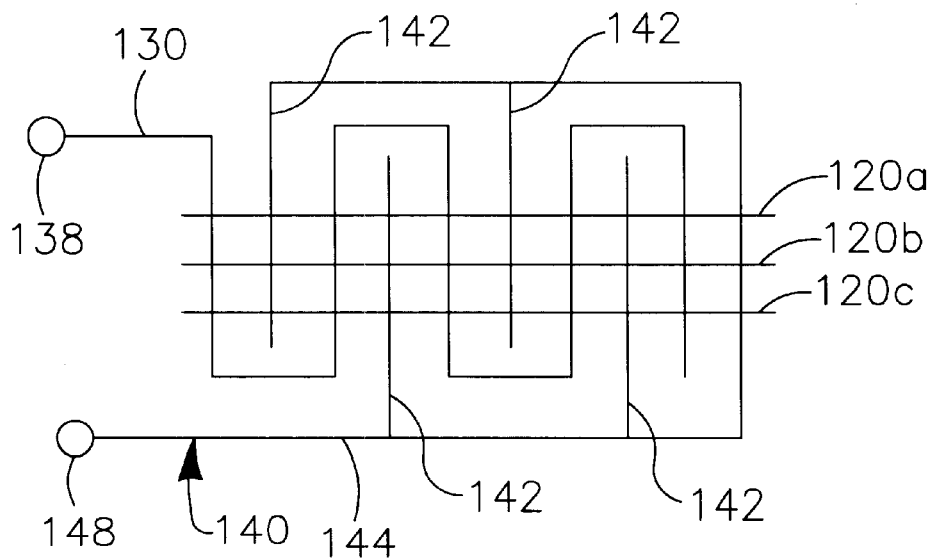
FIG. 4 illustrates another sensor array according to the present invention.

Although one illustrative sensor array 10 is depicted in FIG. 1, alternative array designs are possible. One such alternative is depicted in FIG. 4, in which a single comb electrode 140 is provided with tines 142 that extend into the U-shaped segments of the serpentine electrode 130 opening to both sides of the receptor material lines 120a, 120b, 120c (collectively referred to as lines 120). As a result, the spine 144 of the comb electrode 140 extends around a significant portion of the serpentine electrode 130. The tines 142 intersect the lines 120 of receptor material along with the serpentine electrode 130. Both the illustrated serpentine electrode 130 and the illustrated comb electrode 140 terminate in optional connection pads 138 and 148, respectively, for connection to a detector (not shown).

Figure 5:
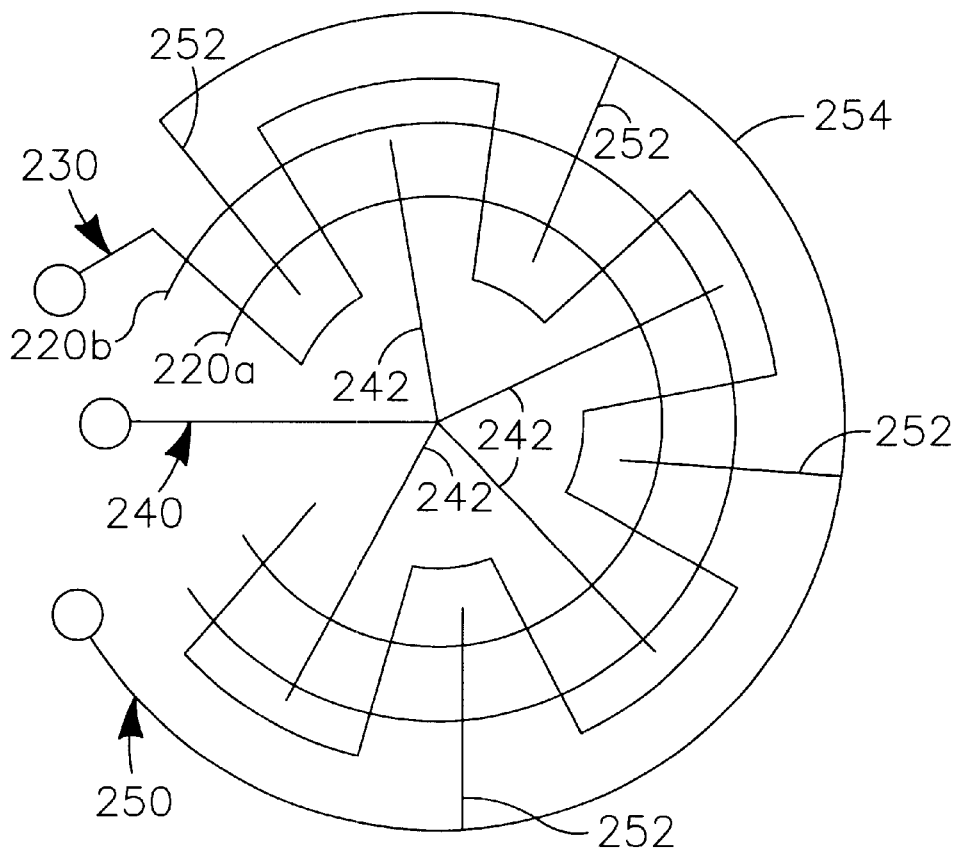
FIG. 5 illustrates another sensor array according to the present invention.

Another alternative array design is depicted in FIG. 5 in which the receptor material lines 220a and 220b (collectively referred to as lines 220) are provide in a generally circular shape. The array includes a serpentine electrode 230 that also includes U-shaped segments opening towards both opposing sides of the lines 220. The array also includes a comb electrode 240 with tines 242 extending into the U-shaped segments from the within the generally circular lines 220, with the tines 242 intersecting with the lines 220 in those U-shaped segments. A second comb electrode 250 is also seen in FIG. 5 that includes tines 252 extending into the U-shaped segments that open outwardly. The tines 252 are connected by a spine 254 that extends about the exterior of the serpentine electrode 230.

Figure 6:
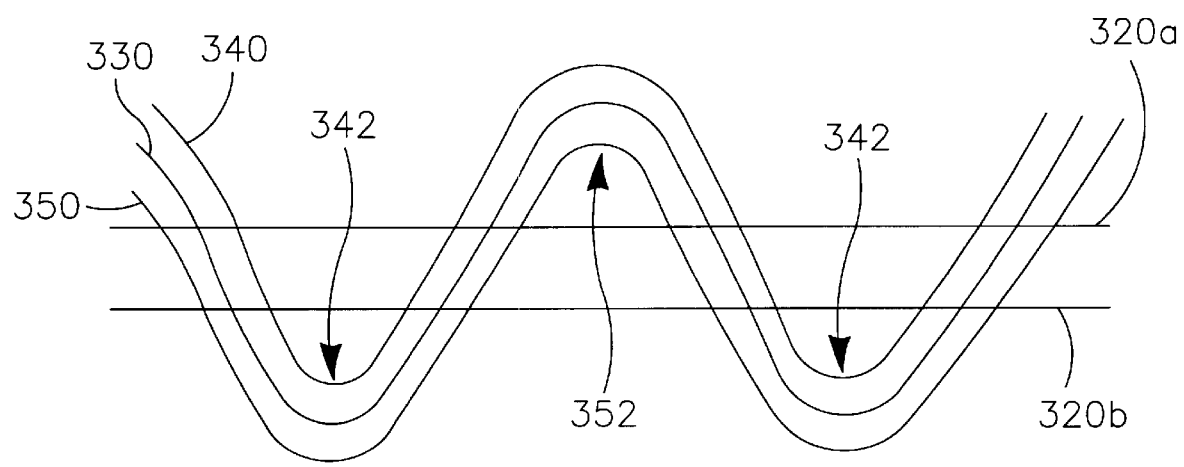
FIG. 6 illustrates another sensor array according to the present invention.

FIG. 6 depicts another illustrative sensor array design in which a sinusoidal serpentine electrode 330 extends along receptor material lines 320a and 320b (collectively referred to as lines 320). The U-shaped segments of the serpentine electrode 330 are, in this embodiment, provided by the sinusoidal wave pattern. The array includes a pair of comb electrodes 340 and 350 that conform to the shape of the sinusoidal serpentine electrode 330 and that also cross the receptor material lines 320. One variation depicted in this array design is that the tines 342 and 352 of the comb electrodes 340 and 350 (respectively) may be provided as portions of a continuous line forming the entire electrode 340 or 350, rather than terminating line segments connected to a spine as depicted in FIGS. 1–5.

One illustrative method of detecting a gas phase material will now be described with respect to ruthenium oxide, although it should be understood that the methods of the present invention may be used to detect a variety of other gas phase materials. Other gas phase materials that could be detected by the devices and methods of the present invention include any gas phase material that deposits on a receptor material in the form of an electrically conductive film or coating.

It will be understood that the composition of the gas phase material will typically correspond to the composition of the film or coating, but that the exact compositions may be different. For example, gas phase ruthenium tetraoxide ($RuO_4$) can be detected based on a film or coating including elemental ruthenium (Ru) and/or ruthenium dioxide ($RuO_2$), both of which are electrically conductive. Examples of other gas phase materials that can be detected according to the principles of the present invention include, but are not limited to, $IrO_4$ and $RhO_4$.

Ruthenium tetraoxide can be deposited by chemical vapor deposition (CVD) which is defined as the formation of a nonvolatile solid film on a substrate by reaction of vapor phase reactants, i.e., reacting gases, that contain desired components.

In a CVD process, the reacting gases are introduced into the reaction chamber. The gas is decomposed and reacted at a heated wafer surface to form the desired layer. Chemical vapor deposition is just one process of providing thin layers on substrate assemblies and other surfaces, such as films of elemental metals or compounds, e.g., platinum, ruthenium, ruthenium oxide, etc. The CVD process may be enhanced by various related techniques such as plasma assistance, photo assistance, laser assistance, as well as other techniques.

The CVD process for depositing ruthenium and/or ruthenium oxide is conducted with a ruthenium containing precursor being delivered to a reaction chamber. Diluent gases may also optionally be provided to the reaction chamber. One skilled in the art will recognize that the manner in which the gases are introduced into the reaction chamber may include one of various techniques.

Gas products contained within the CVD system are potentially harmful to personnel located around the equipment. The present invention provides methods of detecting the escape of the selected materials based on their deposition onto a detection surface and the resulting change in the conductivity of the detection surface.

Figure 7:
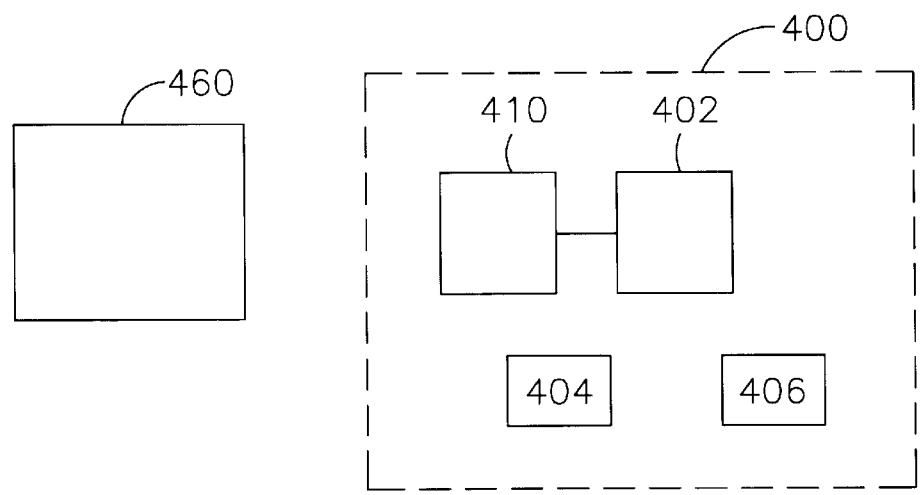
FIG. 7 is a block diagram of a system using a sensor array to detect gas phase materials in accordance with the present invention

Referring to FIG. 7, a sensor 400 according to the present invention is located in proximity to a CVD system 460 in which ruthenium or ruthenium or ruthenium oxide is to be deposited. In some systems, ruthenium oxide may be formed in the CVD system 460 if it is supplied with oxygen in addition to ruthenium for the purpose of forming ruthenium oxide on a substrate.

A sensor 400 according to the present invention, however, may be able to detect gaseous ruthenium oxide that escapes from the system 460. The sensor 400 includes a sensor array 410 and a detector 402 capable of detecting a change in the conductivity between the electrodes on the sensor array 410. The detector 402 preferably includes an electrical circuit capable of detecting the conductivity change between electrodes on the sensor array 410 through the film formed on the receptor materials. If the conductivity reaches a predetermined limit, an alarm 404 can be activated.

If gas phase ruthenium tetraoxide escapes from the CVD system 460, it will typically form ruthenium oxide by oxidation reduction upon contact with the sensor array 410. The deposited film or coating is electrically conductive and, as a result, a change in the conductivity within the array 410 can be used to indicate the presence of ruthenium oxide gas in the area of the sensor 400, thereby alerting personnel in the area or those monitoring an unoccupied area of a potential hazard.

It may be desirable to, e.g., heat the sensor array 410 above the ambient temperature using a heater 406 to potentially enhance sensitivity of the sensor array 410. For example, heating the sensor array 410 may limit deposition of ambient moisture vapor or organic materials present in the atmosphere around the sensor array 410. In the case of ruthenium oxide detection, heating the detection surface up to about 100° C. may be useful to enhance detection.

The heater 406 should be capable of providing thermal energy to the sensor array 410 by any suitable manner including conduction, convection, and/or radiation. In addition, the heater 406 may be an electrical resistance heater, operate using RF excitation, infrared radiation, etc.

It may also be desirable to subject the array 410 to other forms of energy, in addition to or in place of heating, to enhance detection sensitivity. Examples of suitable energy forms include, but are not limited to electromagnetic radiation (visible or not), magnetic fields, etc.

All patents and references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description. It is therefore contemplated that the appended claims will cover any such modifications or embodiments that may fall within the scope of the present invention as defined by the accompanying claims.

What is claimed is:

1. A sensor array for detecting a gas phase material, the array comprising:

a substrate surface;

at least one line of receptor material attached to the substrate surface, wherein the gas phase material, comprising a metallic compound preferentially deposits on the receptor material as compared to the substrate surface surrounding the receptor material;

a serpentine electrode attached to the substrate surface, the serpentine electrode comprising a plurality of U-shaped segments spaced along the line of receptor material and opening in alternating first and second opposing directions along the line of receptor material; and a comb electrode attached to the substrate surface, the comb electrode comprising a plurality of tines, wherein at least some of the tines extend into at least some of the U-shaped segments opening in the first direction, and further wherein at least some of the tines extending into the U-shaped segments intersect the line of receptor material.

2. The sensor array according to claim 1, wherein the serpentine electrode and the comb electrode each comprise a connection pad.

3. The sensor array according to claim 1, wherein the receptor material is located between the substrate surface and the serpentine electrode where the first line and the serpentine electrode intersect.

4. The sensor array according to claim 1, wherein the gas phase material, comprising a metallic compound preferentially deposits on the receptor material as compared to the serpentine electrode and the comb electrode.

5. A sensor array for detecting a gas phase material, the array comprising:

a substrate surface;

at least two lines of receptor material on the substrate surface, wherein the gas phase material, comprising a metallic compound preferentially deposits on the receptor material as compared to the substrate surface surrounding the receptor material;

a serpentine electrode on the substrate surface, the serpentine electrode comprising a plurality of U-shaped segments spaced along the lines of receptor material and opening in alternating first and second opposing directions along the lines of receptor material; and a comb electrode on the substrate surface, the comb electrode comprising a plurality of tines, wherein at least some of the tines extend into at least some of the U-shaped segments opening in the first direction, and further wherein at least some of the tines extending into the U-shaped segments intersect the lines of receptor material.

6. The sensor array according to claim 5, wherein the at least two lines of receptor material do not intersect with each other.

7. The sensor array according to claim 5, wherein the at least two lines of receptor material are generally aligned with and spaced from each other.

8. The sensor array according to claim 5, wherein the at least two lines of receptor material are straight lines parallel to each other.

9. A sensor array for detecting a gas phase material, the array comprising:
   a substrate surface;
   at least one line of receptor material on the substrate surface, wherein the gas phase material, comprising a metallic compound preferentially deposits on the receptor material as compared to the substrate surface surrounding the receptor material;
   a serpentine electrode on the substrate surface, the serpentine electrode comprising a plurality of U-shaped segments spaced along the line of receptor material and opening in alternating first and second opposing directions along the line of receptor material;
   a first comb electrode on the substrate surface, the first comb electrode comprising a plurality of tines, wherein at least some of the tines extend into at least some of the U-shaped segments opening in the first direction, and further wherein at least some of the tines extending into the U-shaped segments intersect the line of receptor material; and
   a second comb electrode on the substrate, the second comb electrode comprising a plurality of tines, wherein at least some of the tines extend into at least some of the U-shaped segments opening in the second direction, and further wherein at least some of the tines of the second comb electrode extending into the U-shaped segments intersect the line of receptor material.

10. The sensor array according to claim 9, wherein the serpentine electrode, the first comb electrode, and the second comb electrode each comprise a connection pad.

11. The sensor array according to claim 9, wherein the first and second comb electrodes are connected to a common connector pad.

12. A sensor array for detecting a gas phase material, the array comprising:
   a substrate surface;
   at least two lines of receptor material on the substrate surface, wherein the selected material preferentially deposits on the receptor material as compared to the substrate surface surrounding the receptor material;
   a serpentine electrode on the substrate surface, the serpentine electrode comprising a plurality of U-shaped segments spaced along the lines of receptor material and opening in alternating first and second opposing directions along the lines of receptor material;
   a first comb electrode on the substrate surface, the first comb electrode comprising a plurality of tines, wherein at least some of the tines extend into at least some of the U-shaped segments opening in the first direction, and further wherein at least some of the tines extending into the U-shaped segments intersect the lines of receptor material; and
   a second comb electrode on the substrate, the second comb electrode comprising a plurality of tines, wherein at least some of the tines extend into at least some of the U-shaped segments opening in the second direction, and further wherein at least some of the tines of the second comb electrode extending into the U-shaped segments intersect the lines of receptor material.

13. An array according to claim 12, wherein the at least two lines of receptor material do not intersect with each other.

14. An array according to claim 12, wherein the at least two lines of receptor material are generally aligned with and spaced from each other.

15. An array according to claim 12, wherein the at least two lines of receptor material are straight lines parallel to each other.

16. An array according to claim 12, wherein the serpentine electrode, the first comb electrode, and the second comb electrode each comprise a connection pad.

17. An array according to claim 12, wherein the first and second comb electrodes are connected to a common connector pad.

18. A method of detecting a gas phase material, the method comprising:
   providing a sensor array comprising:
      a substrate surface;
      at least one line of receptor material on the substrate surface, wherein the gas phase material comprising a metallic compound preferentially deposits on the receptor material as compared to the substrate surface surrounding the receptor material;
      a serpentine electrode on the substrate surface, the serpentine electrode comprising a plurality of U-shaped segments spaced along the line of receptor material and opening in alternating first and second opposing directions along the line of receptor material; and
      a comb electrode on the substrate surface, the comb electrode comprising a plurality of tines, wherein at least some of the tines extend into at least some of the U-shaped segments opening in the first direction, and further wherein at least some of the tines extending into the U-shaped segments intersect the line of receptor material;
   exposing the sensor array to the gas phase material; and
   monitoring electrical conductivity between the serpentine electrode and the comb electrode.

19. A method according to claim 18, further comprising activating an alarm when the electrical conductivity between the serpentine electrode and the comb electrode reaches a predetermined limit.

20. A method according to claim 18, further comprising heating the sensor array.

21. A method according to claim 18, wherein exposing the sensor array to the gas phase material comprises exposing the sensor array to compounds comprising ruthenium.

22. A method of detecting a gas phase material, the method comprising:
   providing a sensor array comprising:
      a substrate surface;
      at least two lines of receptor material on the substrate surface, wherein the gas phase material comprising a metallic compound preferentially deposits on the receptor material as compared to the substrate surface surrounding the receptor material;
      a serpentine electrode on the substrate surface, the serpentine electrode comprising a plurality of U-shaped segments spaced along the lines of receptor material and opening in alternating first and second opposing directions along the lines of receptor material; and a comb electrode on the substrate surface, the comb electrode comprising a plurality of tines, wherein at least some of the tines extend into at least some of the U-shaped segments opening in the first direction, and further wherein at least some of the tines extending into the U-shaped segments intersect the lines of receptor material a substrate surface;

exposing the sensor array to the gas phase material; and monitoring electrical conductivity between the serpentine electrode and the comb electrode.

23. A method according to claim 22, further comprising activating an alarm when the electrical conductivity between the serpentine electrode and the comb electrode reaches a predetermined limit.

24. A method according to claim 22, further comprising heating the sensor array.

25. A method according to claim 22, wherein exposing the sensor array to the gas phase material comprises exposing the sensor array to compounds comprising ruthenium.

26. A method of detecting a gas phase material, the method comprising:

providing a sensor array comprising:
a substrate surface;
at least one line of receptor material on the substrate surface,
wherein the gas phase material comprising a metallic compound preferentially deposits on the receptor material as compared to the substrate surface surrounding the receptor material;
a serpentine electrode on the substrate surface, the serpentine electrode comprising a plurality of U-shaped segments spaced along the line of receptor material and opening in alternating first and second opposing directions along the line of receptor material;
a first comb electrode on the substrate surface, the first comb electrode comprising a plurality of tines, wherein at least some of the tines extend into at least some of the U-shaped segments opening in the first direction, and further wherein at least some of the tines extending into the U-shaped segments intersect the line of receptor material; and
a second comb electrode on the substrate, the second comb electrode comprising a plurality of tines, wherein at least some of the tines extend into at least some of the U-shaped segments opening in the second direction, and further wherein at least some of the tines of the second comb electrode extending into the U-shaped segments intersect the line of receptor material;

exposing the sensor array to the gas phase material; and monitoring electrical conductivity between the serpentine electrode and at least one of the first and second comb electrodes.

27. A method according to claim 26, further comprising activating an alarm when the electrical conductivity between the serpentine electrode and at least one of the first and second comb electrodes reaches a predetermined limit.

28. A method according to claim 26, further comprising heating the sensor array.

29. A method according to claim 26, wherein exposing the sensor array to the gas phase material comprises exposing the sensor array to compounds comprising ruthenium.

30. A method of detecting a gas phase material, the method comprising:

providing a sensor array comprising:
a substrate surface;
at least two lines of receptor material on the substrate surface, wherein the selected material preferentially deposits on the receptor material as compared to the substrate surface surrounding the receptor material;
a serpentine electrode on the substrate surface, the serpentine electrode comprising a plurality of U-shaped segments spaced along the lines of receptor material and opening in alternating first and second opposing directions along the lines of receptor material;
a first comb electrode on the substrate surface, the first comb electrode comprising a plurality of tines, wherein at least some of the tines extend into at least some of the U-shaped segments opening in the first direction, and further wherein at least some of the tines extending into the U-shaped segments intersect the lines of receptor material; and
a second comb electrode on the substrate, the second comb electrode comprising a plurality of tines, wherein at least some of the tines extend into at least some of the U-shaped segments opening in the second direction, and further wherein at least some of the tines of the second comb electrode extending into the U-shaped segments intersect the lines of receptor material;

exposing the sensor array to the gas phase material; and monitoring electrical conductivity between the serpentine electrode and at least one of the first and second comb electrodes.

31. A method according to claim 30, further comprising activating an alarm when the electrical conductivity between the serpentine electrode and at least one of the first and second comb electrodes reaches a predetermined limit.

32. A method according to claim 30, further comprising heating the sensor array.

33. A method according to claim 30, wherein exposing the sensor array to the gas phase material comprises exposing the sensor array to compounds comprising ruthenium.

34. A system for detecting a gas phase material, the system comprising:

a sensor array comprising:
a substrate surface;
at least one line of receptor material on the substrate surface, wherein the gas phase material comprising a metallic compound deposits on the receptor material as compared to the substrate surface surrounding the receptor material;
a serpentine electrode on the substrate surface, the serpentine electrode comprising a plurality of U-shaped segments spaced along the line of receptor material and opening in alternating first and second opposing directions along the line of receptor material; and
a comb electrode on the substrate surface, the comb electrode comprising a plurality of tines, wherein at least some of the tines extend into at least some of the U-shaped segments opening in the first direction, and further wherein at least some of the tines extending into the U-shaped segments intersect the line of receptor material; and a detector in electrical communication with the serpentine electrode and the comb electrode.

35. A system according to claim 34, further comprising a heater.

36. A system for detecting a gas phase material, the system comprising:
- a sensor array comprising:
  - a substrate surface;
  - at least two lines of receptor material on the substrate surface, wherein the gas phase material comprising a metallic compound referentially deposits on the receptor material as compared to the substrate surface surrounding the receptor material;
  - a serpentine electrode on the substrate surface, the serpentine electrode comprising a plurality of U-shaped segments spaced along the lines of receptor material and opening in alternating first and second opposing directions along the lines of receptor material; and
  - a comb electrode on the substrate surface, the comb electrode comprising a plurality of tines, wherein at least some of the tines extend into at least some of the U-shaped segments opening in the first direction, and further wherein at least some of the tines extending into the U-shaped segments intersect the lines of receptor material a substrate surface; and
- a detector in electrical communication with the serpentine electrode and the comb electrode.

37. A system according to claim 36, further comprising a heater.

38. A system for detecting a gas phase material, the system comprising:
- a sensor array comprising:
  - a substrate surface;
  - at least one line of receptor material on the substrate surface, wherein the gas phase material comprising a metallic compound preferentially deposits on the receptor material as compared to the substrate surface surrounding the receptor material;
  - a serpentine electrode on the substrate surface, the serpentine electrode comprising a plurality of U-shaped segments spaced along the line of receptor material and opening in alternating first and second opposing directions along the line of receptor material;
  - a first comb electrode on the substrate surface, the first comb electrode comprising a plurality of tines, wherein at least some of the tines extend into at least some of the U-shaped segments opening in the first direction, and further wherein at least some of the tines extending into the U-shaped segments intersect the line of receptor material; and
  - a second comb electrode on the substrate surface, the second comb electrode comprising a plurality of tines, wherein at least some of the tines extend into at least some of the U-shaped segments opening in the second direction, and further wherein at least some of the tines of the second comb electrode extending into the U-shaped segments intersect the line of receptor material; and
- a detector in electrical communication with the serpentine electrode, the first comb electrode and the second comb electrode.

39. A system according to claim 38, farther comprising a heater.

40. A system for detecting a gas phase material comprising a metallic compound, the system comprising:
- a sensor array comprising:
  - a substrate surface;
  - at least two lines of receptor material on the substrate surface, wherein the selected material preferentially deposits on the receptor material as compared to the substrate surface surrounding the receptor material;
  - a serpentine electrode on the substrate surface, the serpentine electrode comprising a plurality of U-shaped segments spaced along the lines of receptor material and opening in alternating first and second opposing directions along the lines of receptor material;
  - a first comb electrode on the substrate surface, the first comb electrode comprising a plurality of tines, wherein at least some of the tines extend into at least some of the U-shaped segments opening in the first direction, and further wherein at least some of the tines extending into the U-shaped segments intersect the lines of receptor material; and
  - a second comb electrode on the substrate, the second comb electrode comprising a plurality of tines, wherein at least some of the tines extend into at least some of the U-shaped segments opening in the second direction, and further wherein at least some of the tines of the second comb electrode extending into the U-shaped segments intersect the lines of receptor material; and
- a detector in electrical communication with the serpentine electrode, the first comb electrode and the second comb electrode.

41. A system according to claim 40, further comprising a heater.

42. A sensor comprising:
- a substrate surface;
- receptor material in at least one predetermined area attached to the substrate surface, wherein the substrate surface surrounds the at least one predetermined area of receptor material and gas phase material preferentially deposits on the receptor material as compared to the substrate surface;
- a serpentine electrode comprising U-shaped segments spaced along the at least one predetermined area of receptor material; and
- a comb electrode comprising a plurality of tines, wherein at least some of the tines extend into at least some of the U-shaped segments to intersect the receptor material.

43. The sensor of claim 42, wherein the at least one predetermined area is completely surrounded by the substrate surface.

44. The sensor of claim 42, wherein a portion of the receptor material is between the substrate surface and the serpentine electrode where the receptor material and the serpentine electrode intersect, and between the substrate surface and the comb electrode where the receptor material and the comb electrode intersect.

45. The sensor of claim 42, wherein the receptor material comprises at least two predetermined areas of receptor material, and the serpentine electrode intersects the at least two predetermined areas of receptor material and the comb electrode intersects the at least two predetermined areas of receptor material.

46. The sensor of claim 45, wherein the at least two predetermined areas of receptor material are separated by the substrate surface.

47. The sensor of claim 42, wherein the serpentine electrode and the comb electrode intersect the receptor material in multiple locations to form a sensor array.

48. The sensor of claim 42, wherein the receptor material preferentially binds ruthenium compounds.

49. The sensor of claim 42, wherein the substrate surface allows migration of the gas phase material comprising a metallic compound deposited on the substrate surface to the receptor material.

50. A system comprising:
- a sensor, the sensor comprising:
  - a substrate surface;
  - receptor material in at least one predetermined area on the substrate surface, wherein the substrate surface surrounds the at least one predetermined area of receptor material and gas phase material comprising a metallic compound preferentially deposits on the receptor material as compared to the substrate surface;
  - a serpentine electrode comprising U-shaped segments spaced along the at least one predetermined area of receptor material;
  - a comb electrode comprising a plurality of tines, wherein at least some of the tines extend into at least some of the U-shaped segments to intersect the receptor material; and
- a detector in electrical communication with the serpentine electrode and the comb electrode, wherein the detector generates an alert based on deposits of the gas phase material on the sensor.

51. The system of claim 50, wherein, the detector generates the alert when a film of the gas phase material comprising a metallic compound forms on the receptor material.

52. A method, comprising:
- depositing at least one predetermined area of receptor material on a substrate surface, where the substrate surface surrounds the predetermined area of receptor material and gas phase material comprising a metallic compound preferentially deposits on the receptor material as compared to the substrate surface;
- forming a serpentine electrode on the substrate surface, where the serpentine electrode comprises U-shaped segments spaced along the predetermined area of the receptor material; and
- forming a comb electrode on the substrate surface, where the comb electrode comprises a plurality of tines, wherein at least some of the tines extend into at least some of the U-shaped segments opening to intersect the receptor material.

53. The method of claim 52, comprising selecting a distance between the serpentine electrode and the comb electrode to control sensitivity to the gas phase materials.

54. The method of claim 52, comprising selecting the receptor material on which ruthenium compounds and ruthenium oxide preferentially deposit.

55. The method of claim 52, comprising selecting the substrate surface that exhibits a tendency to allow migration of the gas phase material to the receptor material.

56. A method, comprising:
- providing a sensor comprising:
  - a substrate surface;
  - receptor material in at least one predetermined area on the substrate surface, wherein the substrate surface surrounds the at least one predetermined area of receptor material and gas phase material comprising a metallic compound preferentially deposits on the receptor material as compared to the substrate surface;
  - a serpentine electrode comprising U-shaped segments spaced along the at least one predetermined area of receptor material;
  - a comb electrode comprising a plurality of tines, wherein at least some of the tines extend into at least some of the U-shaped segments to intersect the receptor material;
- exposing the sensor to a gas phase material, wherein the gas phase material forms a conductive film on the receptor material; and
- monitoring electrical conductivity between the serpentine electrode and the comb electrode.

57. The method of claim 56, further comprising activating an alarm when the electrical conductivity between the serpentine electrode and the comb electrode reaches a predetermined limit.

* * * * *

UNITED STATES PATENT AND TRADEMARK OFFICE
CERTIFICATE OF CORRECTION

PATENT NO. : 6,479,297 B1
DATED : November 12, 2002
INVENTOR(S) : Sandhu

It is certified that error appears in the above-identified patent and that said Letters Patent is hereby corrected as shown below:

Title page,
Item [56], References Cited,
U.S. PATENT DOCUMENTS, please insert
-- 4,442,422, 04/10/84, Murata et al. --;
-- 4,911,892, 03/27/90, Grace et al. --;
-- 5,331,287, 07/19/94, Yamagishi et al. --;
-- 5,337,018, 08/09/94, Yamagishi --;
-- 5,756,879, 05/26/98, Yamagishi et al. --;
FOREIGN PATENT DOCUMENTS, please insert
-- 1,151,482, 05/07/69, Great Britain --;
-- 1,576,658, 08/01/69, France --;
-- 2-293644, 12/04/90, Japan --;
-- 386,660, 09/12/90, EP --;
-- 3-48748, 03/01/91, Japan --;
OTHER PUBLICATIONS, please insert
-- Bardin et al., "Voltammetry of Ruthenate, Determination of Ruthenium from the Electrochemical Reduction of Ruthenium," *Journal of Analytical Chemistry of the USSR*; 30, 1975: 642-645. --;
-- Bates et al., "The Influence of the electrodeposition parameters on the morphology of organo-transition metal complexes for thin film gas sensor application," *Thin Solid Films*; 299, 1997:18-24 --;
-- Miyashita, Haruzo, "Particle Measurement in Vacuum Tools by In Situ Particle Monitor," *Aneruba Giho*;2, 1996: 67-71 --;

Column 9,
Line 2, please delete ";" and insert -- . --;

Column 12,
Lines 25 and 50, please delete "material," and insert -- material --;
Line 57, please delete "material;" and insert -- material --;

Column 13,
Line 19, please delete "material," and insert -- material --;

UNITED STATES PATENT AND TRADEMARK OFFICE
CERTIFICATE OF CORRECTION

PATENT NO. : 6,479,297 B1
DATED : November 12, 2002
INVENTOR(S) : Sandhu

It is certified that error appears in the above-identified patent and that said Letters Patent is hereby corrected as shown below:

Column 14,
Lines 8, 11, 14, 17 and 20, please delete "An array" and insert -- The sensor --;

Signed and Sealed this

Twenty-sixth Day of August, 2003

JAMES E. ROGAN
*Director of the United States Patent and Trademark Office*